United States Patent [19]

Vogl et al.

[11] Patent Number: 5,099,027
[45] Date of Patent: Mar. 24, 1992

[54] 2(2-HYDROXYPHENYL)2H-BENZO-TRIAZOLE COMPOUNDS AND HOMOPOLYMERS OR COPOLYMERS THEREOF

[75] Inventors: Otto Vogl, New Rochelle, N.Y.; Chongli Zhang, Beijing, China

[73] Assignee: PPG Industries, Inc., Pittsburgh, Pa.

[21] Appl. No.: 246,038

[22] Filed: Sep. 15, 1988

Related U.S. Application Data

[63] Continuation of Ser. No. 84,540, Aug. 12, 1987, abandoned.

[51] Int. Cl.$^5$ .................. C07D 249/16; C08F 26/06
[52] U.S. Cl. .................. 548/259; 548/260; 526/259; 524/94
[58] Field of Search .................. 548/259, 260; 524/94; 526/259

[56] References Cited

U.S. PATENT DOCUMENTS

| | | | |
|---|---|---|---|
| 3,493,539 | 2/1970 | Skoultchi | 526/259 |
| 4,220,788 | 9/1980 | Bader et al. | 548/259 |
| 4,716,234 | 12/1987 | Dunks | 526/259 |

FOREIGN PATENT DOCUMENTS

| | | |
|---|---|---|
| 2333305 | 1/1975 | Fed. Rep. of Germany . |
| 2734149 | 2/1978 | Fed. Rep. of Germany . |
| 2943166 | 5/1980 | Fed. Rep. of Germany . |
| 3231455 | 3/1983 | Fed. Rep. of Germany . |
| 3237004 | 4/1983 | Fed. Rep. of Germany . |
| 3421812 | 12/1984 | Fed. Rep. of Germany . |
| 3428601 | 2/1985 | Fed. Rep. of Germany . |
| 3609504 | 10/1986 | Fed. Rep. of Germany . |
| 1560664 | 3/1969 | France . |
| 2237912 | 2/1975 | France . |
| 73/9147 | 12/1974 | Netherlands . |
| 1407670 | 9/1975 | United Kingdom . |

OTHER PUBLICATIONS

Monatshefte fur Chemie, 115, 853-868 (1984).
Mackromol. Chem., 185, 2497-2509 (1984).
Polymer, 26, 1288-1296 (1985).

*Primary Examiner*—Joseph L. Schofer
*Assistant Examiner*—Peter D. Milcahy
*Attorney, Agent, or Firm*—William J. Uhl

[57] ABSTRACT

Polymerizable ethylenically unsaturated monomers comprising the reaction product of a 1,2-epoxy group-containing polymerizable ethylenically unsaturated monomer and a 2(2-hydroxyphenyl)2H-benzotriazole compound of the structure:

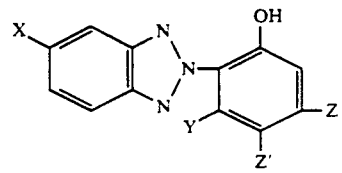

where X is=to H, OR and $NR_2$ where R=alkyl; Z'=H and $C_2H_4OH$; Z and Y=H when Z'=$C_2H_4OH$; when Z'=H, Y and Z=OH or Y=H and Z×OH are disclosed. The monomers are useful in preparing free radical initiated addition polymers. Polymers can also be prepared by first preparing a free radical initiated addition polymer derived from a 1,2-epoxy group-containing polymerizable ethylenically unsaturated monomer and subsequently reacting the polymer with the benzotriazole compound. Both types of polymer contain permanent polymer-bound ultraviolet light stabilizers and are useful as binders for exterior coatings, as resins for the manufacture of optical lenses, and as components for sunscreens and suntanning lotions.

2 Claims, No Drawings

2(2-HYDROXYPHENYL)2H-BENZOTRIAZOLE COMPOUNDS AND HOMOPOLYMERS OR COPOLYMERS THEREOF

This application is a continuation of application Ser. No. 84,540, filed Aug. 12, 1987 now abandoned.

BACKGROUND OF THE INVENTION

1. Field of the Invention

The present invention relates to polymerizable ethylenically unsaturated monomers containing benzotriazole groups and to polymers containing such groups.

2. Brief Description of the Prior Art

Acrylic polymers which are utilized as the resinous component for externally exposed plastics are often light sensitive and must be protected from ultraviolet light in order to prevent degradation of the polymer in the final product. Typically, materials known as ultraviolet light stabilizers are combined with the acrylic polymer to protect the polymer from the effects of ultraviolet light. A particularly well-known group of ultraviolet stabilizers are benzotriazole compounds, particularly those based on 2(2-hydroxyphenyl)2H-benzotriazole. However, UV light stabilizers of this type are often lost from the product into which they are incorporated by leaching or by evaporation.

To overcome these difficulties, efforts have been directed towards chemically incorporating the ultraviolet light stabilizer into the polymeric backbone of the material to be protected. A number of polymerizable ultraviolet stabilizers of the 2(2-hydroxyphenyl)2H-benzotriazole types have been synthesized. For example, 5-vinyl and 5-isopropenyl derivatives of 2(2-hydroxyphenyl)2H-benzotriazole and 4-acrylates or 4-methacrylates of 2(2,4-dihydroxyphenyl)2H-benzotriazole or 2(2,4-dihydroxyphenyl)1,3-2H-dibenzotriazole have been prepared and copolymerized with polymerizable alpha, beta-ethylenically unsaturated monomers to form acrylic polymers containing polymeric bound ultraviolet stabilizers. The 4-acrylates or 4-methacrylates of 2(2,4-dihydroxyphenyl)2H-benzotriazole, although being readily prepared and extremely reactive with other polymerizable alpha, beta-ethylenically unsaturated monomers, are suspect for the possibility of hydrolytic instability because of the presence of the aromatic ester group.

Therefore it is object of the present invention to prepare acrylate and methacrylate esters of 2(2-hydroxyphenyl)2H-benzotriazole derivatives where the 2(2-hydroxyphenyl)2H-benzotriazole units are connected to the acrylate or methacrylate groups by aliphatic ester linkages. These polymeric reaction products should have good hydrolytic stability.

SUMMARY OF THE INVENTION

This invention relates to polymerizable ethylenically unsaturated monomers comprising the reaction product of a 1,2-epoxy group-containing ethylenically unsaturated monomer such as glycidyl methacrylate and a 2(2-hydroxyphenyl)2H-benzotriazole compound of the formula:

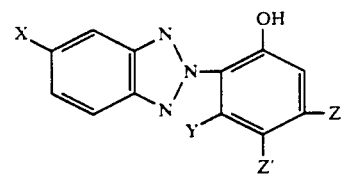

where X=H, OR and NR$_2$ where R is alkyl; Z'=H and C$_2$H$_4$OH; Z and Y=H when Z'=C$_2$H$_4$OH; when Z'=H, Y and Z=OH, or Y=H and Z=OH. The monomers can be homopolymerized or copolymerized with other polymerizable alpha, beta-ethylenically unsaturated monomers to form polymers with permanent polymer bound ultraviolet stabilizers.

Also, polymers can be prepared by first preparing a polymer derived from a 1,2-epoxy group-containing polymerizable ethylenically unsaturated monomer including a homopolymer thereof or a copolymer derived from such a monomer with other copolymerizable ethylenically unsaturated monomers. The polymer can then be reacted with the benzotriazole compounds described above.

DETAILED DESCRIPTION

The polymerizable ethylenically unsaturated monomers of the invention can be prepared by reacting a 1,2-epoxy group-containing polymerizable ethylenically unsaturated monomer and a 2(2-hydroxyphenyl)2H-benzotriazole compound of the formula:

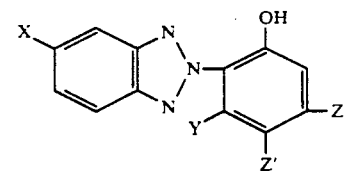

where X is selected from the class consisting of H, OR and NR$_2$ where R is alkyl containing from 1 to 12 carbon atoms, preferably lower alkyl containing from 1 to 4 carbon atoms; Z' is H and C$_2$H$_4$OH, Z and Y are H when Z' is C$_2$H$_4$OH; when Z' is H, Y and Z are OH or Y is H and Z is OH.

Among the 1,2-epoxy group-containing polymerizable ethylenically unsaturated monomers which can be used are glycidyl acrylate, glycidyl methacrylate and allyl glycidyl ether, with glycidyl acrylate and methacrylate being preferred.

The benzotriazole compounds can be prepared by techniques known in the art. See, for example, Monatshefte fur Chemie 115, 853-868 (1984) and Mackromol. Chem. 185, 2497-2509 (1984). Basically, o-nitrobenzenediazonium chloride is condensed with the corresponding phenol followed by reductive cyclization of the initially obtained azo compound with zinc and sodium hydroxide. Among the benzotriazole compounds which may be used in the practice of the invention include 4(2H-benzotriazole-2-yl)1,3-dihydrobenzene (BDH), 4-(5-methoxy-2H-benzotriazole-2-yl)resorcinol (MBDH), 4-(5-methoxy-2H-benzotriazole-2-yl)phloroglucinol and 2(2-hydroxy-5-hydroxyethyl-phenyl)2H-benzotriazole.

The polymerizable ethylenically unsaturated monomer can be prepared by mixing the epoxy-monomer and polymerizable benzotriazole compound together and heating them in the presence of catalyst and an inhibitor to prevent free radical polymerization. Examples of suitable catalysts include acid and base catalyst which are known to catalyze the opening of an epoxide ring by a nucleophile and quaternary ammonium salts which are preferred. Examples of quaternary ammonium salts are tetralkylammonium halides, particularly tetrabutylammonium bromide, benzyltrimethylammonium chloride, benzyltrimethylammonium phosphate and benzyltriethylammonium chloride. Typically, the catalyst is used in amounts of about 0.1 to 5 percent by weight based on total weight of epoxy-monomer containing benzotriazole compound. Examples of suitable free radical inhibitors are hydroquinone, which is preferred and para-methoxyphenol.

Typically the inhibitor is used in amounts of about 0.1 to 2 percent by weight based on total weight of the epoxy-monomer.

Usually, the ingredients are dissolved in an organic solvent such as an aromatic solvent, for example benzene or toluene, and heated together at a temperature of about 50° to 120° C. for about 0.5 to 20 hours. Preferably, the reaction is conducted at about 70°–100° C. for 1 to 15 hours.

The epoxy-monomer and benzotriazole compound are usually present at equimolar ratios. Although excess epoxy monomer or excess benzotriazole compound can be used, there is no real advantage in varying from equimolar ratios. It is believed that the benzotriazole compound which contains a nucleophile such as the non hindred 4-hydroxy group as opposed to the stearically hindered 2-hydroxy group ring opens the epoxide with the nucleophile. It is believed the hydroxy associated with the hydroxyethyl group reacts in the same manner.

After the polymerizable ethylenically unsaturated monomer as described above has been prepared, it can be homopolymerized or copolymerized with other co-polymerizable ethylenically unsaturated monomers to form the permanent polymer bound ultraviolet stabilizer. Examples of other copolymerizable ethylenically unsaturated monomers which may be used include alkyl esters of acrylic and methacrylic acid containing from 1 to 12 carbon atoms in the alkyl group. Specific examples of suitable esters are methyl methacrylate, butyl acrylate, butyl methacrylate and 2-ethylhexyl acrylate. Also, substituted esters such as hydroxyethyl methacrylate and hydroxypropyl acrylate can be used. Examples of other copolymerizable ethylenically unsaturated monomers include vinyl aromatic compounds such as styrene and vinyl toluene. Mixtures of other copolymerizable ethylenically unsaturated monomers may also be used.

The amount of comonomer to be reacted with the polymerizable ethylenically unsaturated monomer of the present invention will depend principally on the amount of the benzotriazole derivative desired in the final polymer product. In general, the comonomer when used can amount to about 5 to 99.99 mole percent by weight based on total moles of the comonomer and the polymerizable ethylenically unsaturated monomer.

Polymerization can be conducted by heating a solution of the polymerizable ethylenically unsaturated monomer of the invention either alone or in combination with the other copolymerizable ethylenically unsaturated monomers in the presence of a free radical initiator for a time sufficient to complete the polymerization. Examples of suitable free radical initiators are those which are soluble in organic solvent and include azo compounds which are preferred such as azobisisobutyronitrile, azobis(alpha,gamma-methylvaleronitrile); peroxide type initiators such as tertiarybutyl perbenzoate and tertiarybutyl peracetate can be used but they are not preferred. Typically, the initiator is present in amounts of about 0.2 to 2 percent by weight based on total weight of polymerizable ethylenically unsaturated monomers.

Usually, the polymerizable ethylenically unsaturated monomers and initiator are dissolved in an organic solvent for the polymerization, although solvent is not required. Examples of suitable organic solvents include aromatic solvents include aromatic solvents such as benzene and toluene and polar organic solvents such as N,N-dimethylacetamide (DMAc). Mixtures of solvents can also be used. The amount of organic solvent which is used can vary from about 0.05 to 80 percent by weight based on total weight of the solution.

The time and temperature for the polymerization can vary within wide ranges depending principally on what initiators used. Typically, polymerization is conducted for about 0.5 to 20 hours at about 60° to 100° C.

Besides polymerizing the ethylenically unsaturated monomer containing the benzotriazole groups with other polymerizable ethylenically unsaturated monomers as described above, polymers can also be prepared by reacting preformed 1,2-epoxy group-containing acrylic polymers with the benzotriazole compounds as described above. The 1,2-epoxy group-containing acrylic polymer can be prepared by polymerizing 1,2-epoxy group-containing monomers with other copolymerizable ethylenically unsaturated monomers. Examples of 1,2-epoxy group-containing monomers are those described above, namely, allyl glycidyl ether, glycidyl acrylate and glycidyl methacrylate. Examples of the other copolymerizable monomers are also those such as described above, that is, alkyl acrylates and methacrylates containing from 1 to 12 carbon atoms in the alkyl group and the vinyl aromatic compounds.

The amounts of the 1,2-epoxy monomer and the other copolymerizable monomers can vary over fairly wide ranges. Typically, the amount of the epoxy monomer will constitute from 0.01 to 95 mole percent of all the copolymerizable ethylenically unsaturated monomer content. Conditions for polymerization are also as generally described above, that is, the monomers along with a suitable initiator are dissolved in an organic solvent and polymerized by heating the solution. Examples of suitable initiators are the azo compounds and the peroxide compounds described above. Suitable solvents include aromatic compounds such as toluene and benzene. The time and temperature for polymerization is typically from about 0.5 to 20 hours at a temperature of 60 to 100° C. Besides solution polymerization, suspension and emulsion polymerization can also be used.

After the 1,2-epoxy group-containing acrylic polymer has been prepared, it is allowed to react with the benzotriazole containing nucleophile, typically by mixing the polymer and the benzotriazole compound together and heating in the presence of a suitable catalyst. Examples of suitable catalysts include the quaternary ammonium salts described above. Typically the catalyst is used in amounts of about 0.1 to 5 percent by weight based on total weight of polymer and benzotriazole compound. Usually, the reactive ingredients and catalyst are dissolved in an organic solvent to facilitate the reaction. Examples of suitable organic solvents are aromatic solvents such as benzene and toluene and polar organic solvents such as N,N'-dimethyl acetamide. Mixtures of such solvents can also be used. Typically, the solvent is used in amounts of about 0.2 to 80 percent by weight based on total weight of the solution. The time and temperature of the reaction will, in general, vary from about 0.5 to 20 hours at a temperature of 50° to 120° C., preferably 1 to 15 hours at 70° to 100° C. The amounts of the benzotriazole compounds and the copolymer which are allowed to react with one another will depend on how much of the benzotriazole compound is desired in the final reaction product and also on the 1,2-epoxy content of the copolymer. Typically, the amounts are adjusted such that the final polymeric product will contain from about 0.01 to 95 mole percent of the benzotriazole derivative in the polymeric reaction product.

The polymeric reaction products prepared as described above which contain the polymer bond benzotriazole derivatives make excellent UV light stabilizers for coating applications, that is, the polymers can be used by themselves, as binders for organic coatings, or they can be used as components along with other resinous materials in the coating formulation. The polymers can also be used either by themselves or in combination with other polymeric materials in the manufacture of lenses for optical use. The products can also be used as components for sunscreens and suntanning lotions.

The present invention will be further illustrated by the following examples which are provided for the purpose of illustration only and are not intended to limit the present invention. Unless otherwise indicated, all percentages are by weight.

EXAMPLE 1

The following example shows the preparation of 2[2-hydroxy-4-alkoxy-(2-oxypropyl-α-methylacrylate)-phenyl]2H-benzotriazole (BDHG):

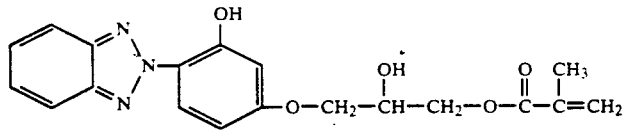

Into a round bottom flask equipped with a condenser were added 2.21 g, 0.01 mole of 4(2H-benzotriazole-2-yl)1,3-dihydrobenzene (BDH), 1.71 g, 0.012 mole of glycidyl methacrylate, 0.08 g of tetrabutylammonium bromide, 10 mg of hydroquinone and 6 ml of a 1:1 mixture of benzenetoluene. The mixture was stirred at 80°-85° C. for 12 hours. The reaction product was then washed three times each with 100 ml of water and separated. The solvent was then removed on a rotating evaporator. The crude reaction product was recrystallized from methanol to yield a white powder having a melting point of 112°-114° C. The yield was 56 percent. Elemental analysis indicated 61.22 percent carbon, 5.02 percent hydrogen and 11.45 percent nitrogen as compared to calculated values of 61.79 percent, 5.15 percent and 11.38 percent, respectively.

EXAMPLE 2

The following example shows the preparation of 2[2-hydroxy-4-alkoxy-(2-oxypropyl-α-methylacrylate)-phenyl]2H-4-methoxybenzotriazole (MBDHG):

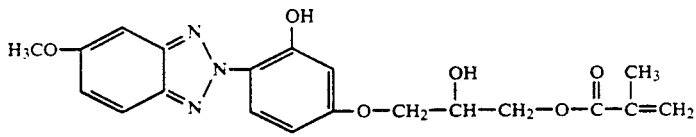

Into a round bottom flask equipped with a condenser were added 5.16 g, 0.02 moles of 4-(5-methoxy-2H-benzotriazole-2-yl)resorcinol (MBDH), 3.42 g, 0.024 moles of glycidyl methacrylate, 0.17 g of tetrabutylammonium bromide, 20 mg of hydroquinone and 8 ml of benzene. The mixture was stirred at 80° C. for 14 hours. The reactant was washed three times with 200 ml of water and separated. The benzene was then removed on a rotating evaporator. Ten (10) ml of carbon tetrachloride was added and the reaction mixture cooled. A solid reaction product was filtered and dried. The crude product was recrystallized from methanol-carbon tetrachloride (1:1) to yield a white powder having a melting point of 100°-102° C. The yield was 30 percent. Elemental analysis indicated 59.69 percent carbon, 5.3 percent hydrogen and 10.87 percent nitrogen as compared to calculated values of 60 percent, 5.25 percent and 10.50 percent, respectively.

EXAMPLE 3

The following example shows the homopolymerization of BDHG prepared in Example 1.

Into a 5 ml polymerization tube was placed 1.3 mg of azobisisobutyronitrile, 0.74 g, 2 mmol of BDHG and 2 ml of N,N-dimethylacetamide (DMAc). The tube was sealed and heated to 70° C. and held at this temperature for 6 hours. The tube was then opened and the rebutyronitrile, diluted by pouring slowly into 200 ml of methanol. The polymer precipitated was filtered and dried at 50° C. under vacuum for one day. A 68 percent yield of (poly-BDHG) was obtained.

EXAMPLE 4

The following example shows the homopolymerization of MBDHG. Into a 5 ml polymerization tube was placed 1.3 mg of azobisisobutyronitrile, 0.80 g of MBDH and 2 ml of DMAc. The tube was sealed and heated to 70° C. and held at this temperature for 6 hours. The tube was opened and the reaction mixture poured slowly into 200 grams of methanol. The polymer precipitated was filtered and dried at 50° C. under vacuum for one day. The poly-MBDHG was obtained in 84 percent yield.

EXAMPLE 5

The following example shows the copolymerization of BDHG with methyl methacrylate.

Into a 10 ml polymerization tube was charged 8 mg of azobisisobutyronitrile, 0.74 g, 2 mmol of BDHG, 1.00 g, 10 mmol of methyl methacrylate and 2 ml of DMAc. The tube was sealed and heated to 70° C. and held at this temperature for 6 hours. The reaction tube was opened, the reaction mixture diluted with 10 ml of acetone and the diluted mixture poured slowly into 200 ml of methanol. The copolymer precipitated was filtered and dried at 50° C. under vacuum for one day. The copolymer was obtained in 78 percent yield. The resulting copolymer contained 31.7 mole percent BDHG as determined by elemental analysis of nitrogen.

EXAMPLE 6

The following example shows the copolymerization of BDHG with styrene.

Into a 10 ml polymerization tube was placed 8 mg of azobisisobutyronitrile, 0.74 g, 2 mmol of BDHG, 1.04 g, 10 mmol of styrene and 2 ml of DMAC. The tube was sealed and heated to 70° C. and held at this temperature for 6 hours. The tube was opened and the reaction mixture diluted with 10 ml of acetone and the diluted reaction mixture poured slowly into 200 ml of methanol. The copolymer precipitated, was filtered and dried at 50° C. under vacuum for one day. The copolymer, styrene-BDHG, was obtained in 55 percent yield. The polymer contained 38 mole percent BDHG as determined by elemental analysis of nitrogen.

EXAMPLE 7

The following example shows copolymerization of MBDHG with methyl methacrylate.

The copolymerization was conducted generally in accordance with the procedure of Example 5 above with the exception that 0.4 g, 1.0 mmol of MBDHG and 0.5 g, 5.0 mmol of methyl methacrylate were used. The copolymer was obtained in 86 percent yield. The polymer contained 41 mole percent MBDHG unit as determined by elemental analysis of nitrogen.

EXAMPLE 8

The following example shows copolymerization of MBDHG with styrene. The copolymerization was conducted as generally described above for Example 6 with the exception that 0.40 g, 1.0 mmol of MBDHG and 0.52 g, 5.0 mmol of styrene were used. Also, the polymerization was conducted at 70° C. for 20 hours. The resulting copolymer was obtained in 45 percent yield and contained 51 percent MBDHG unit as determined by elemental analysis of nitrogen.

EXAMPLE 9

The following example shows the preparation of a copolymer of glycidyl methacrylate and methyl methacrylate which was then allowed to react with BDH.

Into a 20 ml pyrex polymerization tube were placed 3.6 g, 36 mmol of methyl methacrylate, 0.57 g, 4 mmol of glycidyl methacrylate and 13 mg of azobisisobutyronitrile dissolved in 2 ml of benzene. The tube was degassed, sealed and heated to 70° C. and held at this temperature for 4 hours. The tube was opened and the reaction mixture diluted with 10 ml of acetone and poured into 200 ml of methanol. The copolymer precipitated, was filtered and dried at 0.1 mm Hg for one day. The yield was 90 percent.

Into a 25 ml reaction flask equipped with a stirrer was added 1.04 g, 10 mmol of the copolymer, 0.23 g, 1 mmol of BDH, 50 mg of tetrabutylammonium bromide and 6 ml of a 1:1 DMAc-benzene solvent mixture. The reaction mixture was stirred at 70° C. for 4 hours. The reaction mixture was diluted with 10 ml of benzene and poured slowly into 200 ml of methanol. A white powder precipitated which was washed with 50 ml of methanol, collected by filtration and dried at 60° C. for 2 days. The copolymer contained 18.6 mole percent BDH.

EXAMPLE 10

The following example shows the preparation of a copolymer of glycidyl methacrylate and methyl methacrylate followed by reaction with MBDH. A glycidyl methacrylate-methyl methacrylate copolymer was prepared as generally described above in Example 9.

Into a 25 ml reaction flask equipped with a stirrer was added 1.02 g, 10 mmol of the copolymer, 0.13 g, 0.5 mmol of MBDH, 50 mg of tetrabutylammonium bromide and 6 ml of a 1:1 DMAc-benzene solvent mixture. The reaction mixture were stirred at 70° C. for 4 hours. The reaction product was diluted with 10 ml of acetone and poured slowly into 200 ml of methanol. A white powder precipitated which was washed with 50 ml of methanol, collected by filtration and dried at 60° C. for 2 days. The copolymer contained 12.6 mole percent MBDH.

EXAMPLE 11

The following example shows the preparation of a copolymer of styrene and glycidyl methacrylate which was further reacted with BDH.

Into a 20 ml pyrex polymerization tube were placed 3.74 g, 36 mmol of styrene 0.57 g, 4.0 mmol of glycidyl methacrylate, 13 mg of azobisisobutyronitrile dissolved in 2 ml of benzene. The tube was degassed, sealed and heated to 70° C. and held at this temperature for 2 hours. The tube was opened and the reaction mixture diluted with 10 ml of acetone and poured into 200 ml of methanol. The polymer precipitated, was filtered and dried at 0.1 mm Hg for one day. The yield was 69 percent.

Into a 25 ml reaction flask equipped with a stirrer were added 1.06 g, 10 mmol of the styrene-GMA copolymer, 0.11 g, 0.5 mmol of BDH, 50 mg of tetrabutylammonium bromide and 4 ml of a 1:1 DMAc-benzene solvent mixture. The reaction mixture was stirred at 70° C. for 4 hours. The reaction product was diluted with 10 ml of acetone and poured slowly into 200 ml of methanol. A white powder precipitated which was washed with 50 ml of methanol, collected by filtration and dried at 60° C. for 2 days. The copolymer contained 15 mole percent BDH.

EXAMPLE 12

The following example shows the preparation of a copolymer of glycidyl methacrylate and styrene followed by reaction with MBDH. The glycidyl methacrylate-styrene copolymer was prepared as generally described above in Example 11.

Into a 25 ml reaction flask equipped with a stirrer was added 1.06 g, 10 mmol of the copolymer, 0.13 g, 0.5 mmol of MBDH, 50 mg of tetrabutylammonium bromide and 4 ml of a 1:1 DMAc-benzene solvent mixture. The reaction mixture was stirred at 70° C. for 4 hours. The reaction mixture was diluted with 10 ml of acetone and poured slowly into 200 ml of methanol. A white powder precipitated which was washed with 50 ml of methanol, collected by filtration and dried at 60° C. for 2 days. The copolymer contained 15 mole percent of MBDH.

We claim:

1. A polymerizable ethylenically unsaturated monomer comprising the reaction product of a 1,2-epoxy group-containing polymerizable ethylenically unsaturated monomer and a 2(2-hydroxyphenyl)2H-benzotriazole compound of the formula:

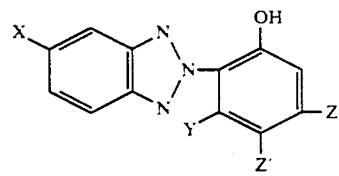

where $X=H$; $Z'=H$ and $C_2H_4OH$; Y and $Z=H$ when $Z'=C_2H_4OH$; when $Z'=H$, Y and $Z=OH$.

2. The monomer of claim 1 in which the 1,2-epoxy group-containing polymerizable ethylenically unsaturated monomer is glycidyl methacrylate.

* * * * *

UNITED STATES PATENT AND TRADEMARK OFFICE
CERTIFICATE OF CORRECTION

PATENT NO. : 5,099,027
DATED : March 24, 1992
INVENTOR(S) : Otto Vogl et al It is certified that error appears in the above-identified patent and that said Letters Patent is hereby corrected as shown below:

In the Abstract on the cover page, the chemical structure should read:

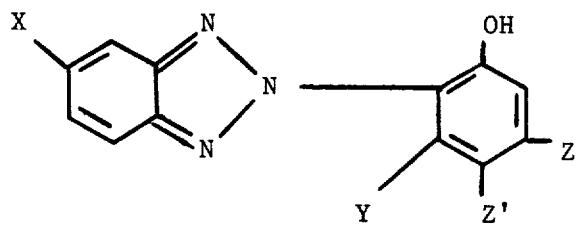

In the Abstract on the cover page, third line after the chemical structure, "Z X OH" should read --Z = OH--.

At the top of column 10, the chemical structure should read:

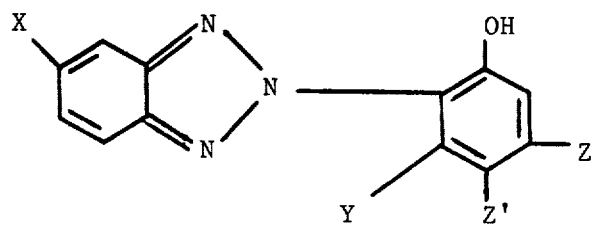

Signed and Sealed this

First Day of June, 1993

Attest:

MICHAEL K. KIRK

Attesting Officer

Acting Commissioner of Patents and Trademarks